US00PP36222P2

(12) United States Plant Patent
Vermeulen et al.

(10) Patent No.: US PP36,222 P2
(45) Date of Patent: Oct. 22, 2024

(54) ***DRACAENA* PLANT NAMED 'JANET LINDO'**

(50) Latin Name: ***Dracaena steudneri* Schweinf. ex Engl.**
Varietal Denomination: JANET LINDO

(71) Applicants: Joost Vermeulen, Lubbeek (BE); Mathijs Vermeulen, Lubbeek (BE)

(72) Inventors: Joost Vermeulen, Lubbeek (BE); Mathijs Vermeulen, Lubbeek (BE)

( * ) Notice: Subject to any disclaimer, the term of this patent is extended or adjusted under 35 U.S.C. 154(b) by 0 days.

(21) Appl. No.: 18/445,498

(22) Filed: Sep. 1, 2023

(51) Int. Cl.
*A01H 5/12* (2018.01)
*A01H 6/12* (2018.01)

(52) U.S. Cl.
USPC ..... Plt./383

(58) Field of Classification Search
USPC ..... Plt./383
CPC ..... A01H 5/12; A01H 5/00; A01H 6/12
See application file for complete search history.

(56) References Cited

U.S. PATENT DOCUMENTS

PP17,913 P2 * 8/2007 Berlin ..... A01H 6/12
Plt./383

OTHER PUBLICATIONS

Upov Pluto 20231130 retrieved on Nov. 28, 2023 at https://pluto.upov.int/result, one page. (Year: 2023).*

* cited by examiner

*Primary Examiner* — June Hwu
(74) *Attorney, Agent, or Firm* — Samuel R. McCoy, Jr.

(57) ABSTRACT

A new and distinct Dracaena plant named 'JANET LINDO' which is characterized by broadly lorate foliage borne on a short, unbranched stem, foliage with the central portion of the lamina colored green to greyed-green foliage and longitudinally striped with fine light-green stripes, foliage that is colored with a mixture of yellow-green and yellow at the marginal zones, narrowly margined with a combination of dark green and greyed-green, and the stability of these characteristics from generation to generation.

2 Drawing Sheets

Latin name of the genus and species: The Latin name of the genus and species of the novel variety disclosed herein is *Dracaena steudneri* Schweinf. ex Engl.

Variety denomination: The inventive cultivar of *Dracaena* disclosed herein has been given the variety denomination 'JANET LINDO'.

BACKGROUND OF THE INVENTION

Parentage: 'JANET LINDO' is a spontaneous branch mutation of an unnamed *Dracaena steudneri* plant (not patented) which typified the species. The mutation was discovered at a commercial greenhouse in Lubbeek, Belgium in March of 2018. The mutation was initially noted for its dark green foliage with broad yellow margins. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'JANET LINDO' is accomplished by way of rooting stem cuttings. Propagation was first performed in March of 2018 at the inventor's commercial greenhouse in Lubbeek, the Netherlands. Through five subsequent generations, the unique features of this cultivar have proven to be stable and true to type.

SUMMARY OF THE INVENTION

The cultivar 'JANET LINDO' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'JANET LINDO'. These characteristics in combination distinguish 'JANET LINDO' as a new and distinct *Dracaena steudneri* cultivar:

1. *Dracaena* 'JANET LINDO' exhibits broadly lorate foliage that is borne on a short, unbranched stem; and
2. *Dracaena* 'JANET LINDO' exhibits foliage with the central portion of the lamina colored green to greyed-green foliage and longitudinally striped with fine light-green stripes; and
3. *Dracaena* 'JANET LINDO' exhibits foliage that is very broadly margined with a mixture of yellow-green and yellow.

BOTANICAL DESCRIPTION OF THE PLANT

Figure 1:
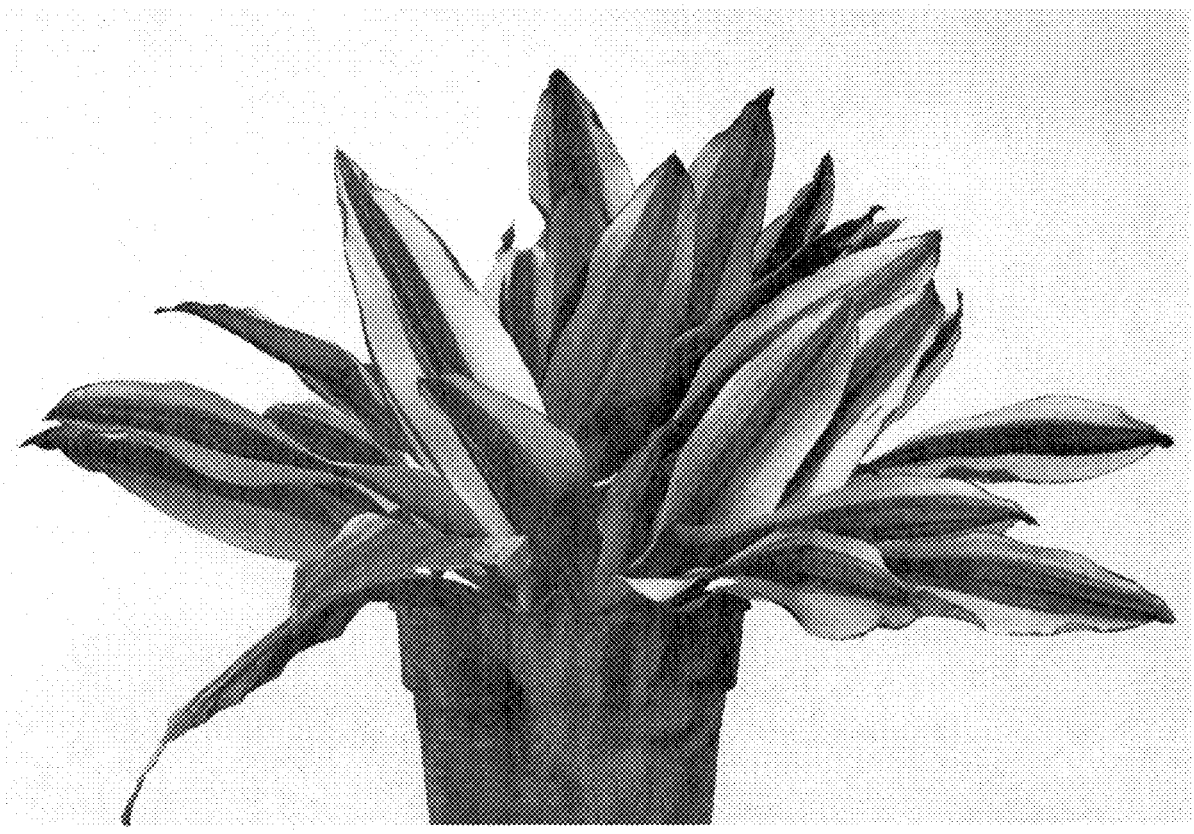
FIG. 1 illustrates, as nearly true as it is reasonably possible to make the same in color photographs of this type, an exemplary plant of 'JANET LINDO' grown in Lubbeek, Belgium. This plant, grown in a 17 cm nursery container, is approximately 1.5 years old from a rooted young plant.
Figure 2:
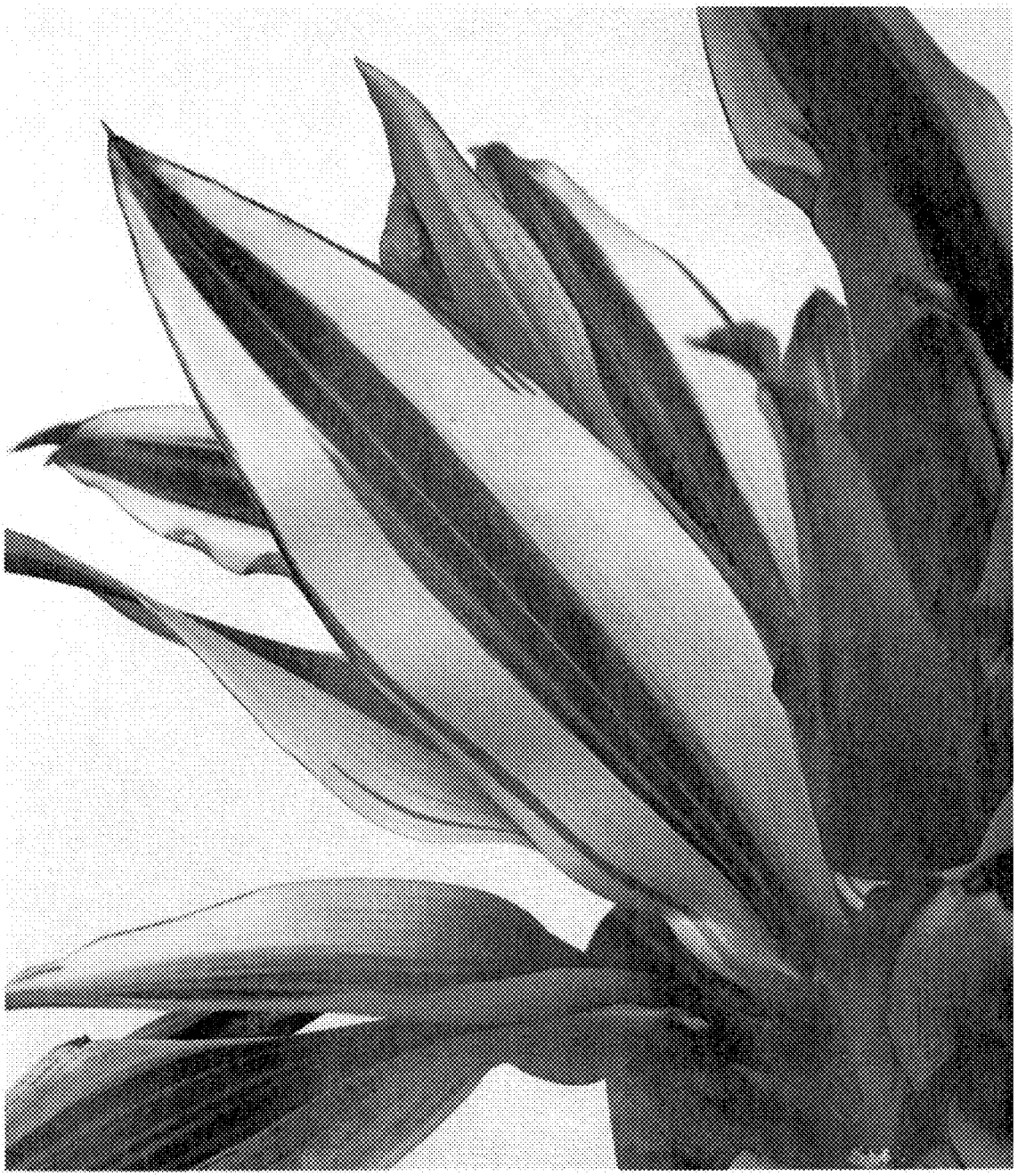
FIG. 2 illustrates, as nearly true as it is reasonably possible to make the same in color photographs of this type, the typical foliage of 'JANET LINDO'.

The following observations and measurements, made in July of 2022, describe averages from a sample set of six specimens of 1.5-year-old 'JANET LINDO' plants grown in 17 cm nursery pots in San Jose, Costa Rica. Plants were produced using conventional greenhouse production protocols for *Dracaena* sp. which consisted of growing under shade cloth, regular overhead irrigation, and chemical control of thrips insects. No photoperiodic treatments or artificial light was given to the plants.

Those skilled in the art will appreciate that certain characteristics will vary with older or, conversely, with younger plants. 'JANET LINDO' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'JANET LINDO' and comparisons with the parent plant and most similar commercial *Dracaena* cultivar known to the inventor are provided below.

Plant description:

*Growth habit*.—Compact, upright evergreen perennial with foliage born on a solitary short, unbranched stem.

*Plant profile*.—Broad obovate.

*Average height from base to top of foliage*.—28.7 cm.

*Average width*.—Average of 49.2 cm.

*Plant Vigor*.—Moderately vigorous.

*Propagation Details*.—Asexual propagation is accomplished by stem cuttings.

*Time to initiate roots*.—Approximately 3 weeks are required to initiate roots at 20 degrees Celsius.

*Time to produce a marketable* 12 *cm potted plant*.—Approximately 10 weeks.

*Disease and pest resistance or susceptibility*.—Neither tolerance nor resistance to normal diseases and pests of *Dracaena steudneri* have been observed.

*Environmental tolerances*.—Adapt to USDA Hardiness Zones 10 through 12 and temperatures as high as 40 degrees Celsius; moderate tolerance to rain and wind.

Root system:

*General*.—Fibrous; freely branched and moderately dense rooting.

*Distribution in the soil profile*.—Shallow to moderately deep.

*Texture*.—Smooth; glabrous.

Stems:

*Branching characteristics*.—Not freely branched in nature; develops lateral branches only when manipulated by man by way of pruning. Naturally produces one main stem arising from the plant's base.

*Attitude*.—Near vertical.

*Strength*.—Very strong.

*Length*.—7.8 cm.

*Diameter*.—Average 1.3 cm.

*Internode length*.—Average 1.3 cm.

*Stem texture*.—Glabrous; smooth.

*Stem luster*.—Slightly glossy.

*Color, developing stems*.—Yellow-green, nearest to RHS 145C.

*Color, mature stems*.—Yellow-green, nearest to a mixture of RHS 145B and 146B.

*Color at the internodes*.—Yellow-green, nearest to RHS 146B.

Foliage:

*Arrangement*.—Alternate.

*Attachment*.—Sheathed.

*Division*.—Simple.

*Attitude*.—Near upright.

*Number of leaves per shoot*.—8.

*Lamina*.—Dimensions — 33.0 cm long and 6.9 cm wide, on average. Shape — Broadly lorate. Aspect — Slightly spiraled, with the distalmost portion on the lamina pointing downward at an average angle of minus-30 degrees to the rest of the lamina. Apex — Acute with a short, pungent tip. Base — Sheathed. Sheath Length — 2.3 cm. Width — 1.35 cm. Color, adaxial surface — Green-white, nearest to RHS 157A. Color, abaxial surface — Green-white, nearest to a mixture of RHS 157A and 157B. Margin — Entire; coarse undulation. Texture and luster of adaxial surface — Smooth, glabrous and slightly glossy. Texture and luster of abaxial surface — Smooth, glabrous and matte. Color — Juvenile foliage, adaxial surface — The central portion of the lamina is green, nearest to a mixture of RHS NN137B and 141A yet darker; broadly margined with a lighter shade of green, nearest to RHS 143A. Juvenile foliage, abaxial surface — The central portion of the lamina is green to yellow-green, nearest to a mixture of RHS 138A and 147B; broadly margined yellow-green, nearest to RHS 146B. Mature foliage, adaxial surface — The central portion of the lamina is colored with a mixture of green and greyed-green, nearest to RHS NN137A and N189A yet darker, with light green longitudinal striping colored nearest to a mixture of RHS 137A and 137D; the marginal zones, comprising approximately two-thirds of the total laminar surface, equal to approximately 2.3 cm in width on either side of the central zone, are colored with a mixture of yellow-green to yellow, RHS 5B, 6C, 151C, and 151D. Random portions of the foliar margins are narrowly and irregularly margined with a combination of green and greyed-green, nearest to RHS NN137A and N189A yet darker. Mature foliage, abaxial surface — The central portion of the lamina is colored with a mixture of green and yellow-green, nearest to RHS 137C and 147B yet darker, with light greyed-green longitudinal striping colored nearest to RHS 191B; the marginal zones, comprising approximately two-thirds of the total laminar surface, equal to approximately 2.3 cm in width on either side of the central zone, are colored with a mixture of yellow-green to yellow, RHS 3C, 151C, 151D, 154C, and 154D. Random portions of the foliar margins are narrowly and irregularly margined with a combination of green and greyed-green, nearest to RHS NN137A and N189A yet darker. Venation — Pattern — Parallel. Color, adaxial surface — The main vein yellow-green, nearest to a mixture of RHS 138B and 147B. All other veins are indistinguishable from the surrounding foliage. Color, abaxial surface — The main vein is yellow-green, nearest to RHS 144A. All other veins are indistinguishable from the surrounding foliage.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

Comparisons with the parent plant: Plants of the new cultivar 'JANET LINDO' may be distinguished from its parent, an unnamed *Dracaena steudneri* plant (not patented), by the characteristics described in Table 1.

TABLE 1

| Characteristic | 'JANET LINDO' | The parent. |
|---|---|---|
| Foliage shape. | Broadly lorate. | Lorate. |
| Foliage aspect. | Spiraled, with the distal portion curling downward. | Straight; not spiraled or curling downward. |
| General coloration of the mature adaxial foliar surface. | Central portion of the lamina is colored with a mixture of green and greyed-green, with light green longitudinal striping; marginal zones, comprising approximately two-thirds of the laminar surface, are colored with a mixture of yellow-green to yellow. Random portions of the foliar margins are narrowly and irregularly margined with a combination of green and greyed-green, nearest to RHS NN137A and N189A yet darker. | Mid-green; broadly and irregularly margined golden yellow. |

Plants of the new cultivar 'JANET LINDO' are similar to the commercial comparator, *Dracaena steudneri* 'SILINDO' (U.S. Pat. application Ser. No. 18/445,497). The two plants may be distinguished from one another by the characteristics described in Table 2.

TABLE 2

| Characteristic | 'JANET LINDO' | 'SLINDO' |
|---|---|---|
| Foliage shape. | Broadly lorate. | Lorate. |
| Foliar margin undulation. | Moderately, coarsely undulating. | Lightly, coarsely undulating. |
| General coloration of the mature adaxial foliar surface. | Central portion of the lamina is colored with a mixture of green and greyed-green, with light green longitudinal striping; marginal zones, comprising approximately two-thirds of the laminar surface, are colored with a mixture of yellow-green to yellow. Random portions of the foliar margins are narrowly and irregularly margined with a combination of green and greyed-green, nearest to RHS NN137A and N189A yet darker. | Yellow-green stripes, generally appearing as golden yellow, are present along the central zone of the lamina. Stripes vary from a plurality of narrow, individual stripes to a single, broad stripe, all running from the base to the apex. Narrowly margined yellow-green, generally appearing as golden yellow. |

Plants of the new cultivar 'JANET LINDO' are also similar to the commercial cultivar, *Dracaena fragrans* 'Sol' (U.S. Pat. No. 17,913). However, the two plants may be distinguished from one another by the characteristics described in Table 3.

TABLE 3

| Characteristic | 'JANET LINDO' | 'Sol' |
|---|---|---|
| Growth rate. | Slower growing than 'Sol', reaching 45 cm tall, with a 7.8 cm long main stem, in a 17 cm nursery container, in 18 months. | Faster growing than 'JANET LINDO', reaching 45 cm tall, with a 15 cm long main stem, in a 17 cm nursery container, in 4 months. |
| Foliage length. | Longer than 'Sol'. | Shorter than 'JANET LINDO'. |
| General coloration of the mature adaxial foliar surface. | Central portion of the lamina is colored with a mixture of green and greyed-green, with light green longitudinal striping; marginal zones, comprising approximately two-thirds of the total laminar surface, are colored with a mixture of yellow-green to yellow. Random portions of the foliar margins are narrowly and irregularly margined with a combination of green and greyed-green, nearest to RHS NN137A and N189A yet darker. | Central portion of the lamina is colored with a combination of green and yellow-green; marginal zones, comprising approximately one-half of the total laminar surface, are colored yellow. Broadly margined green. |

That which is claimed is:

1. A new and distinct cultivar of Dracaena plant named 'JANET LINDO', substantially as described and illustrated herein.

* * * * *